US006861033B2

United States Patent
Mullins et al.

(10) Patent No.: US 6,861,033 B2
(45) Date of Patent: Mar. 1, 2005

(54) PURIFIED WATER SUPPLY SYSTEM FOR HIGH DEMAND DEVICES AND APPLICATIONS

(75) Inventors: Stephen M. Mullins, Lakewood, CO (US); Douglas A. Luehmann, Battle Lake, MN (US); John D. Bielefeld, Prairie Village, KS (US)

(73) Assignee: Gambro, Inc., Lakewood, CO (US)

(*) Notice: Subject to any disclaimer, the term of this patent is extended or adjusted under 35 U.S.C. 154(b) by 0 days.

(21) Appl. No.: 10/709,530

(22) Filed: May 12, 2004

(65) Prior Publication Data

US 2004/0195157 A1 Oct. 7, 2004

Related U.S. Application Data

(62) Division of application No. 10/041,898, filed on Jan. 7, 2002, now abandoned.
(60) Provisional application No. 60/260,036, filed on Jan. 5, 2001.

(51) Int. Cl.[7] .................................................. A61L 2/16
(52) U.S. Cl. ........................ 422/28; 137/14; 137/15.01; 137/563; 137/565.17; 210/90; 210/123; 210/137; 210/167; 210/257.2; 210/764; 422/41
(58) Field of Search ................................ 137/14, 15.01, 137/15.05, 563, 565.11, 565.17, 565.27; 422/1, 28, 41; 210/87, 90, 123, 137, 167, 257.1, 257.2, 646, 741, 767, 805

(56) References Cited

U.S. PATENT DOCUMENTS

| 3,870,033 | A | 3/1975 | Faylor et al. |
| 4,332,264 | A | 6/1982 | Gortz et al. |
| 5,783,072 | A | 7/1998 | Kenley et al. ........... 210/257.1 |
| 6,197,197 | B1 | 3/2001 | Peterson et al. |
| 6,228,255 | B1 | 5/2001 | Peterson et al. ......... 210/257.2 |
| 6,235,199 | B1 | 5/2001 | Peterson et al. |
| 6,251,279 | B1 * | 6/2001 | Peterson et al. ............ 210/636 |
| 6,319,399 | B1 | 11/2001 | Peterson et al. |

OTHER PUBLICATIONS

Selections from a Section 510(k) application for a marketed device (1998–1999).

* cited by examiner

Primary Examiner—Joseph Drodge
(74) Attorney, Agent, or Firm—John R. Merkling; Edna M. O'Connor; Laura M. Butterfield

(57) ABSTRACT

A water supply sub-system for connection to a main water supply system includes a storage tank having an inlet with a flow control valve for connection to the main water supply system. The sub-system may be disconnected from the main system and configured as a closed system for disinfecting the sub-system. An outlet line connects the storage tank to a pump that pumps water from the tank to a sub-system supply line. One or more branch connections may connect the sub-system supply line to high-demand water using devices, such as dialysis machines. The supply line may be a feedback loop. A shunt feedback loop parallel to the feedback loop of the supply line has a pressure control valve that regulates pressure in the supply line feedback loop. A filtration device may also be included to ensure the purity of the water circulating through the sub-system.

21 Claims, 5 Drawing Sheets

PURIFIED WATER SUPPLY SYSTEM FOR HIGH DEMAND DEVICES AND APPLICATIONS

CROSS REFERENCE TO RELATED APPLICATIONS

This application is a divisional of U.S. patent application Ser. No. 10/041,898, filed Jan. 7, 2002, abandoned, which claimed the benefit of provisional application 60/260,036, filed Jan. 5, 2001.

BACKGROUND OF INVENTION

The present invention relates generally to water supply systems, and more particularly to a system adapted for supplying purified water to one or more water using devices, some of which having distinctive water consumption demands, including devices having distinctively and usually intermittently high demands versus devices having low demands for flow rates and/or volumes of purified water. This invention further presents particular advantages in medical and like high quality purified water supply systems such as in allowing for the supply of water to both high demand dialyzer reprocessing machines and lower demand dialysis machines without substantially increasing the total operational volume or flow rate of purified water flowing through the entire water supply system.

There are presently a variety of industrial and medical devices and associated procedures that require the use of purified water. A prominent example is found in medical dialysis. In such dialysis procedures generally, including hemodialysis, hemofiltration and hemodiafiltration processes, blood to be dialyzed is taken from a patient and passed through a dialyzer where the blood is cleaned of its impurities and then returned to the patient. Contemporary dialyzers are ordinarily of a membrane type in which the blood may be passed along one side of the membrane, while in the most common types of dialysis, another liquid, often called dialysate, may be passed along the opposite side of the membrane. This process is conceptually the same in plate, hollow fiber and coil dialyzers. Ideally, impurities in the blood pass from the blood through the membrane and into the liquid dialysate. The liquid dialysate carrying these impurities then flows out of the dialyzer and is usually passed through a dialysis control monitor or machine to a drain. Some types of dialysis also include providing a replacement liquid to the patient, the replacement liquid being passable with the blood through the dialyzer, or otherwise often being infused directly into the blood returning to the patient.

The dialysate and replacement liquids are both generally made from purified water into which various additive solutions and/or powders are mixed to create respective liquid solutions that are usually substantially isotonic to blood. Often this mixing of additives with purified water may be effected at and/or by each discrete dialysis machine (also known as a monitor) during each dialysis session. This process is often referred to as on-line dialysate or replacement liquid preparation. A centralized, substantially continuous supply of purified water may then preferably be presented to one or more of such on-line dialysis machines in a particular setting such as a hospital or a dialysis clinic for the preparation of these respective liquids during operation.

In a centralized water supply system such as this, it is common to provide a centralized purification arrangement including a reverse osmosis (R/O) apparatus or unit and/or a de-ionization (DI) apparatus or unit among other purification devices, such as carbon and/or mechanical filters and/or chemical treatment devices such as water softeners. There may also be additional water treatment for the removal of bacteria and/or endotoxins or the addition of or subjection to electromagnetic waves, e.g., ultraviolet light for the inactivation or destruction of such pathogens. In any event, the R/O or DI unit commonly establishes the last purification step in the purification arrangement which, as is known in the art, then provides output purified water to medically acceptable and/or otherwise preferable or desirable quality or like standards.

As mentioned above, this purified water may then be delivered in a typical dialysis setting to one or a plurality of dialysis machines, preferably through short branch connections emanating from a main or central supply line. The central supply line may then provide for the flow any unused water to a drain or it may form a circuit by feeding back into one or more of the purification devices (such as the R/O unit) for re-purification and/or to other units (such as a central storage tank) and then/thereby provide for recirculation out to and through the central supply line circuit.

Other machines that use purified water have also been known to be commonly connected to such a centralized water supply line. An example particularly fitting within a hospital or dialysis clinic setting is the connection to the purified water circuit of one or more dialyzer re-use machines (also known as dialyzer reprocessing machines). As is understood, dialyzer re-use machines use the purified water to clean dialyzers after respective dialysis sessions for re-use in later dialysis procedures.

One common concern arising from such an incorporation of dialyzer re-use machines is the relatively high water demand such re-use machines usually require to complete their cleaning procedures. Re-use machines normally require a high volume (though usually intermittent) flow rate of water, albeit usually for a short time period when compared with the lower (usually more constant) demand, longer-term dialysis machine use. However, contemporary centralized purified water circuits often have relatively constant maximum output flow rates, depending ordinarily upon the maximum output of the respective R/O unit if, as is common, the R/O unit feeds directly into the main water supply circuit. The high demands of one or more re-use machines connected to a main supply line can then significantly negatively impact a centralized water supply system having an R/O unit which directly feeds water at a constant maximum output. The negative impact of the high demand is such that it may overburden the main water supply system by drawing too much water flow from the main supply line to the point that the flow of purified water provided simultaneously to any other water using machines such as one or more dialysis machines may be reduced, interrupted or the central line pressure may be decreased sufficiently so that one or more of the dialysis machines do not have sufficient water volume or pressure to continue producing dialysate and/or replacement fluid, as needed for the dialysis procedure, and may thus be forced into an alarm state and possible automatic shut-down. Such alarms and possible shut downs may then provide a danger to the dialysis patient(s).

Note, R/O and/or DI feeding into intervening holding tanks is known in the art. However, such tanks have been disposed in the primary water circuit, and as such are often necessarily unacceptably too large (approximately 250 gallons) for many medical/dialysis settings and/or have too many stagnation areas (as in bladder surge tanks) thus providing unacceptable opportunities for undesirable biological and/or microbiological growth. Additionally, these prior holding tank systems must maintain high flow rates throughout their piping systems to maintain turbulent flow, which minimizes bacterial growth. There are usually large pressure drops through such piping systems due to the high flow rates and long lengths of the piping system as well as due to the number of taps for each water using unit to be attached to the piping system. Intermittent high demand devices such as dialyzer re-use equipment draw large amounts of water out of the piping system in a short period of time. This may cause the pressure levels to drop sharply throughout the piping system, thereby likely causing both the re-use equipment and any other attached water-using equipment, such as dialysis machines, to not have sufficient water volume and/or pressure to operate properly.

Other industrial water usage machines and water supply circuits may also suffer similar drawbacks. Such systems may include pharmaceutical preparation processes and/or electronic device (e.g., microchip) manufacturing processes. Thus, any system that may include the use of both low and high water demand devices on a water supply line may take advantage of the present invention.

Hence, a need exists for providing for a safe, non-overburdensome connection of high water demand devices, like dialyzer re-use machines, to a water supply line so that other lower demand machines, such as dialysis machines, may be provided with a sufficient, uninterrupted supply of water volume, pressure and/or flow rates to maintain normal operations. It is toward this and related aims that the present invention is directed.

SUMMARY OF INVENTION

The present invention is directed to the provision of a water supply sub-system, which is connectable to a centralized or main water supply system. The sub-system provides for the connection of one or more relatively high demand water using devices in a substantially isolated or lower demand disposition relative to the main water circuit. Generally, the present sub-system includes a sub-system storage tank, which is connectable to the main water supply system, and a sub-system water line to which the high demand device or devices may be attached. This sub-system water line (also referred to in some recirculatable embodiments as a loop, see below) is connected to and leads from the sub-system storage tank, through a pump to one or more outlet connections for a potential variety of generally high volume flow rate demand, short duration water use devices such as dialyzer re-use machines. This further sub-system water line may be dead ended (thus, no loop), or run to a drain or drain connection, or more preferably, it may feed back to the sub-system storage tank for recirculation therethrough (and, thus form a loop). A shunt line may additionally or alternatively be connected to the sub-system water line to provide pressure control for the output from the pump, and/or for more directly feeding from the pump back to the storage tank for the same or perhaps a similar general recirculation purpose. At least one of these recirculation lines preferably feeds into or near the top of the storage tank and feeds through a spray head arrangement therein (thus completing the loop) which disperses the incoming water in a substantially continual spray configuration to maintain a substantially constant movement, non-stagnating air to water interface within the tank. This assists in maintaining a preferably more sterile environment within the storage tank. The other feedback line may preferably feed into a lower part of the storage tank to counteract vortex action at the tank outlet. A microbiological filter and/or various other components may also be included in or along the sub-system water line to ensure and/or increase operational effectiveness and/or efficiency.

In use, purified water may be taken into the sub-system storage tank from the centralized supply system at a substantially controlled, relatively constant low rate so that a substantially no or low fluctuation demand is presented by the sub-system to the central or main supply system. The tank can then feed a short duration, higher volume flow rate to the rest of the sub-system, which, including one or more high water demand devices, can then draw the respective higher flow, higher volume demands from the outflow of the sub-system storage tank while the storage tank continues to draw the preferably constant, substantially lower maximum volume flow rate from the main supply system. This high demand draw may have the effect of drawing down the total volume contained within the sub-system storage tank, but does so generally for only a comparatively short duration and preferably not to an empty state. The maximum intermittent high demands of the high demand devices may thus be accounted for within the total operating storage tank volume. The high demand devices may then be operated at any time during which the storage tank contains a sufficient residual water volume without then impacting on or interrupting the main supply of water to the lower demand, longer duration dialysis or like machines connected directly to the main line.

As noted, systems of the present invention may be highly beneficial in purified water supply systems such as in medical applications like dialysis, or may also be useful in pharmaceutical preparation or electronics manufacturing or other water supply processes.

These and other aspects of the current invention will become clearer from the description of preferred embodiments considered in conjunction with the attached drawings which are described briefly below.

DETAILED DESCRIPTION

Figure 1:
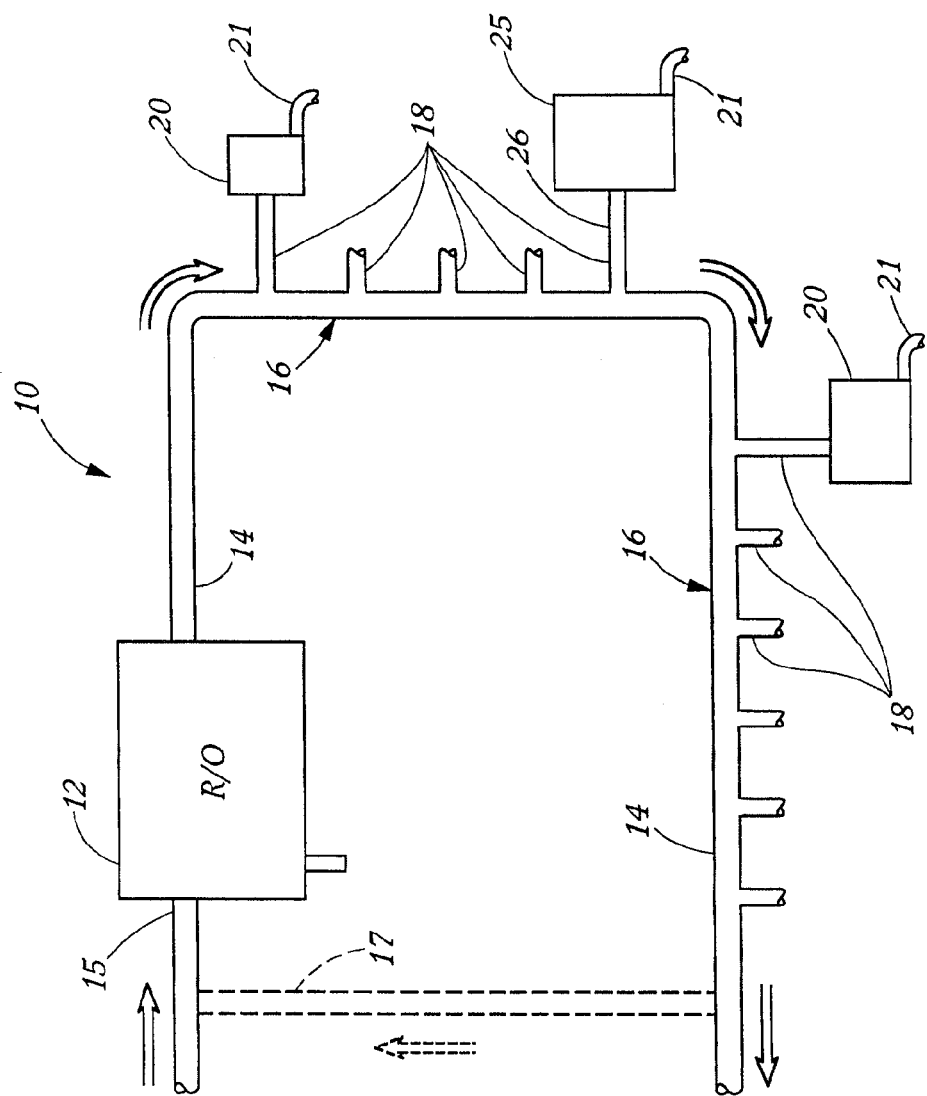
FIG. 1 is a schematic view of a centralized purified water supply system in which the present invention may be incorporated.
Figure 1A:
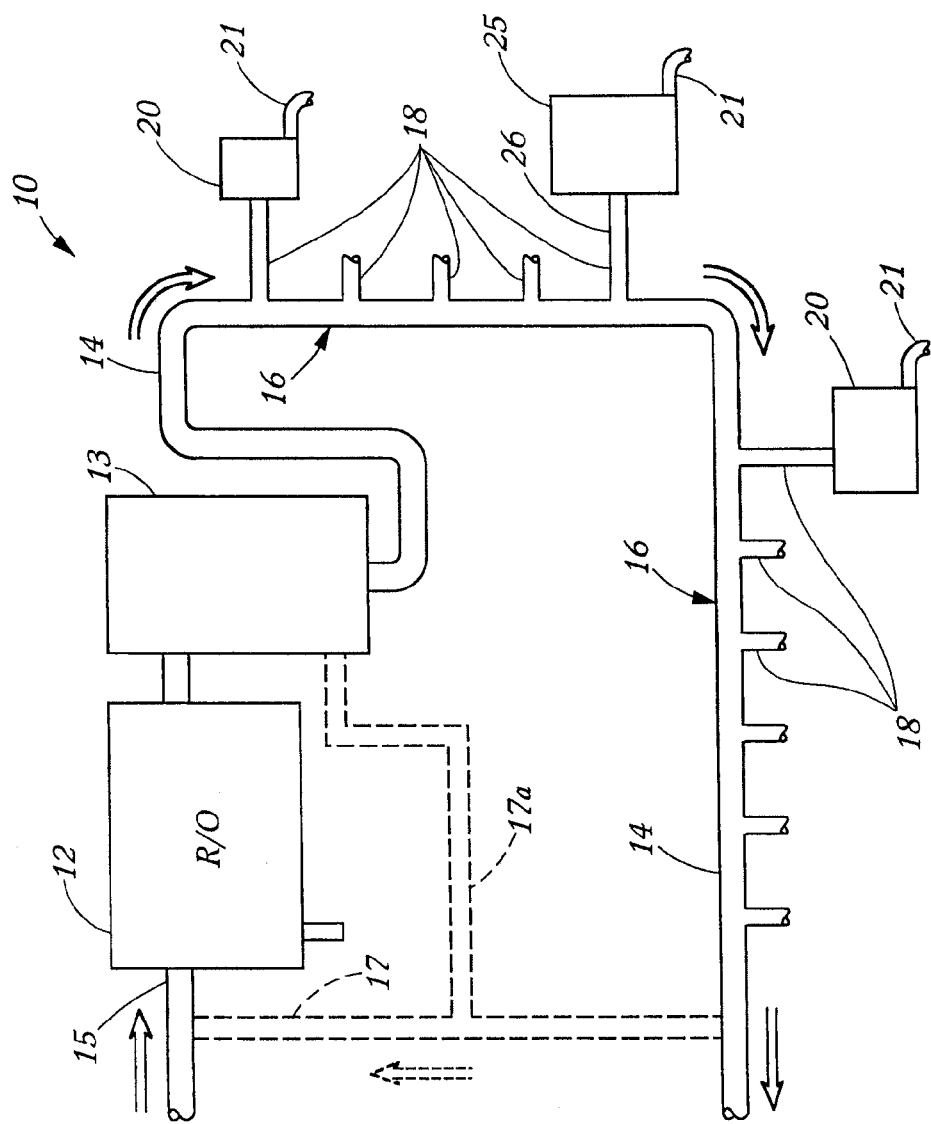
FIG. 1A is a schematic view of an alternative centralized purified water supply system in which the present invention may be incorporated.

A centralized or main water supply system 10 is shown in FIGS. 1 and 1A including a water treatment or purifying unit 12 which feeds purified water either directly into an outlet purified water supply line 14 (FIG. 1) or indirectly to line 14 via an intervening storage tank 13 (FIG. 1A). Unit 12 is preferably here a reverse osmosis (R/O) or de-ionization (DI) unit 12, and either of these or other types of treatment units may be considered here even if R/O is used in the description here. Water line 14 is the distribution line, which may also be referred to as the main line 14 herein to distinguish it from various other water lines to be described throughout this specification. An inlet feed line 15 which feeds into treatment unit 12 will be understood as feeding water from any of various sources or combinations of sources (none shown) such as from a tap and/or from one or more pre-treatment or filtration devices (carbon and/or mechanical filter(s) and/or chemical or water softening or like water treatment device(s), for example, none shown). Moreover, feed line 15 may also alternatively receive feedback water from the purified water line 14 via a connecting line 17 (shown in dashed lines in FIGS. 1 and 1A) to create a main supply circuit or loop 16. An alternative feedback line 17a (FIG. 1A) provides for feedback of water to the storage tank 13, if used.

The water system main line 14 is shown having a plurality of connection branches generally designated in FIG. 1 with the reference numeral 18. One or more water using machines 20 may then be connected through respective branches 18 to the central or main water line 14. In this description particularly of FIG. 1, machines 20 may be considered relatively generically such that they may be understood to represent, for example, one or more dialysis machines, and/or for another example, one or more dialyzer re-use machines, inter alia. As was described hereinabove, it has been known in the art to connect one or more dialysis machines and/or one or more dialyzer re-use machines to a single main water supply line 14. Further devices, machines or outlet taps have been known to be similarly connected to a main line 14 in a dialysis setting as well, including, for example, taps for centralized bicarbonate concentrate preparation, dialyzer pre-rinse or dialyzer cleansing devices (e.g., for cleaning a dialyzer prior to use of the dialyzer in a dialysis process, also referred to as pre-cleaning devices, herein), and/or pre-rinse sensor or sink cleansing devices. Any such devices are intended also to be represented interchangeably by the generic reference numeral 20 in FIG. 1. Water used thereby may then be flowed to a drain via a respective drain line 21. This water may alternatively be returned to the inlet of the treatment unit 12, see line 17 in FIG. 1, or to a central storage tank 13, see FIG. 1A.

Figure 2:
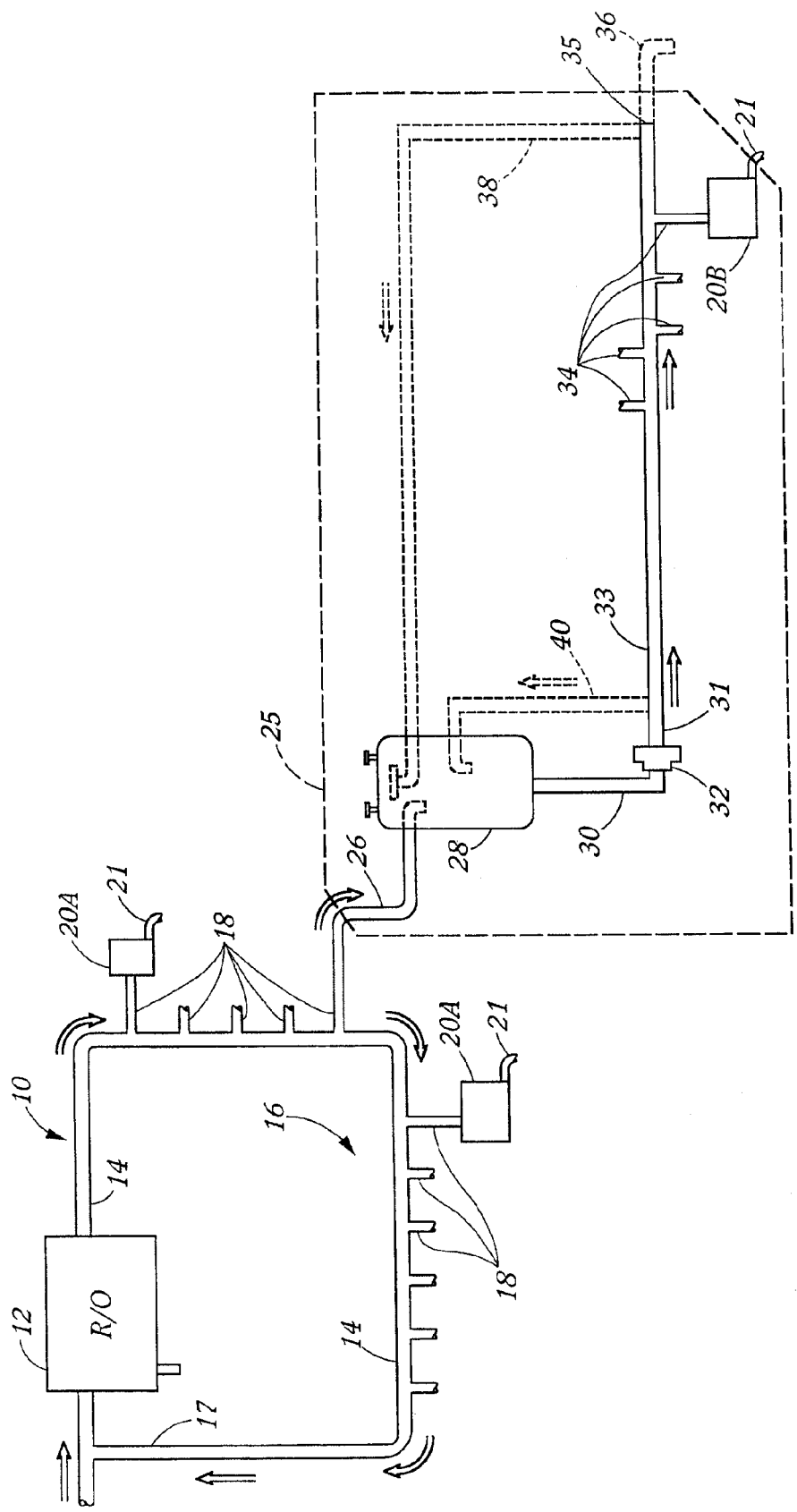
FIG. 2 is a schematic view of a water supply sub-system according to the present invention as connected to the centralized purified water supply system of FIG. 1.

Nevertheless, because of the pressure fluctuations in main line 14 caused by high demand devices, in the present invention, the direct connection of generic water use machines 20 as shown in FIG. 1 to the main line 14 is preferably restricted, as shown more particularly in FIG. 2, to the connection of low water or substantially constant water demand machines 20A (FIG. 2). Thus, the generic water machines 20 of FIG. 1 which are directly connected to main line 14, are hereafter referred to in the present invention as low demand machines 20A (FIG. 2). Low demand machines 20A include, for example, dialysis machines. Higher demand machines 20B (see FIG. 2), such as dialyzer re-use machines will, according to the present invention, be connected to and/or within a water supply sub-system which is identified schematically in FIG. 1 by the box designated 25, and is shown in more detail in FIG. 2 within a dashed box outline similarly identified by the reference numeral 25 therein.

More particularly in FIG. 2, a sub-system inlet line 26 is shown schematically connecting the water supply sub-system 25 to the main line 14 through its connection at one end of line 26 to a main system outlet branch 18 of the main line 14, and at the other end to a sub-system storage tank 28. Emanating from tank 28 is a storage tank outlet line 30, which flows to a pump 32. Pump 32 is preferably of a centrifugal type, which may thus be pressure controlled at the outlet thereof, as will be described below. At the outlet of pump 32 is an outlet line 31 which is connected to or is coincident with a sub-system supply line 33 which provides water to one or more branch connections 34, to which may be connected one or more respective water using machines, such as the representative high-demand machine 20B shown in FIG. 2. Note, tank outlet line 30, pump outlet line 31 and supply line 33 may be separate elements, or they may all be contiguous or coincident with each other (depending upon the pump type used), or in either event, they may be simply considered to comprise a single outlet supply line for simplicity of description.

Also shown in FIG. 2 are three alternative additional flow paths (shown in dashed lines), at least two of which providing preferred alternatives to the dead-ended supply line 33 indicated in FIG. 2 by the dead-end 35 (dead-ended refers to the non-recirculating flow stopping effect the dead-end 35 provides at the end of supply line 33). The first alternative is a drain line 36, which provides a drainage flow path for unused water to flow to a drain (not shown). The second alternative flow path which is presently preferred over or at least in addition to a drain line 36, is a feed-back loop 38 which provides for flowing any unused water back to the storage tank 28 for recirculation as described in more detail relative to FIG. 3 below. The third alternative flow path is provided by a feed back shunt line 40 which is disposed upstream of the branch connections 34 to provide for the alternative of providing pressure regulation and recirculating unused water to the storage tank 28 simultaneously with (or perhaps without) flowing the unused water through the entire loop 38. Preferably, all three alternatives to the dead-end 35 will be provided in sub-system 25. However, any one or more of these alternative flow paths (or none of them, as depicted in FIG. 2) may be disposed in a sub-system 25 according to the present invention and could be simultaneously so connected and may be connected by shutoff or three-way valves or the like (not specifically shown). Any one or more of these flow paths may thus be chosen for directing water flow therethrough at any given time as may be desired. Further examples of such flow choices and the preferred purposes therefor will be described below.

Figure 3:
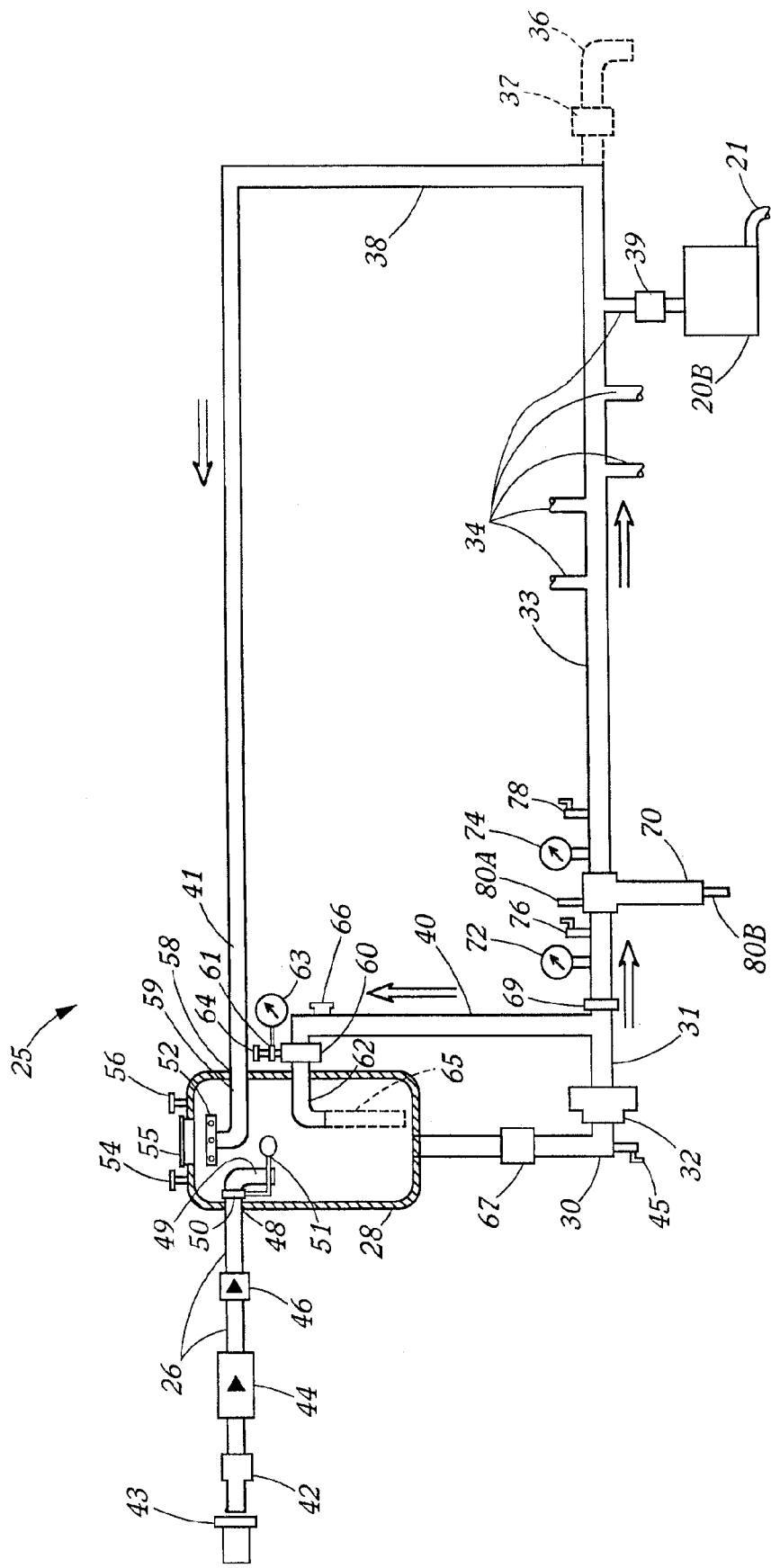
FIG. 3 is an enlarged schematic view of a preferred alternative sub-system according to the present invention, shown detached from a central water supply system.

A further detailed embodiment of a preferred sub-system 25 according to the present invention is shown in FIG. 3. Many of the alternative elements included herein are preferred within the scope of the present invention, but may be added to, substituted for or eliminated as may be appreciated by those skilled in the art. Inlet line 26 preferably also includes a connecting device 42 and one or more valves, preferably a check valve 44 and a flow control valve 46. The connecting device 42 is preferably a male connector, which may or may not include a shut-off which would mate with a female connector 43 which preferably includes a shutoff (not shown) disposed in or attached to the branch 18 or directly emanating from the main line 14 (thus constituting the branch 18, shown schematically in FIG. 1). The check valve 44 maintains flow in one direction from main line 14 to the tank 28 and is preferably disposed adjacent or near the connecting device 42. The flow control valve 46 may be more preferably disposed adjacent the inlet 48 to the storage tank 28. The flow control valve 46 provides for flow rate control into tank 28, and in the preferred embodiment is not variable or operator manipulable. Rather, valve 46 is preferably a manufacturing chosen size based on the maximum burden to be presented by the one or more high demand machines (see 20B) considered in combination with the lowest acceptable main water line supply minimum flow rate with which sub-system 25 may be used. This may thus take into account the quantity and type of lower demand machines (dialysis and the like, e.g.) which may be designed to be connected to the main line 14. Different sized valves 46 could thus be used depending upon the quantities and/or types of lower demand devices 20A might be used, as well as what the operating output of the particular purification unit 12 being used. Valve 46 may also, in a less preferred alternative embodiment, be used to provide manual on/off control of flow into tank 28.

Inside the storage tank 28 (shown in cross-section in FIG. 3), an extension 49 of the inlet line 26 preferably runs from and/or through a float valve 50 to provide inlet flow into tank 28. Water flowing into tank 28 through inlet line 26 would preferably flow through valve 50 and the extension 49 to fill the tank 28. As the tank fills with inlet water to a pre-determined level, the water will move the float arm assemblage 51 upwardly and thereby cause closure of float valve 50 and halt further water inflow into tank 28 through line 26.

Storage tank 28 also preferably has a vent 54, an access port 55 and a disinfectant inlet port 56. Vent 54 is preferably a 0.2 micron porous membrane filter vent to allow air flow therethrough, but not ingress of biological contaminants such as bacteria. Substantially atmospheric operating pressures may thus be achieved within tank 28, though without risk of contamination. Access port 55 allows operator access for manufacturing, maintenance, parts replacement or cleaning as desired, and port 56 provides for flowing disinfectant solution therethrough into tank 28 for disinfection procedures carried out on a preferably regular basis (see description below).

One or more recirculation inlets 58, 68 are preferably also provided in storage tank 28 for connection, as described below, of one or more recirculation loops. The first such feedback loop 38 is connected to tank 28 via a first inlet line 41 through inlet 58. An inlet extension line 59 extends through inlet 58 to provide for communication of recirculation flow into tank 28. As shown, extension line 59 is also preferably connected to the spray head arrangement 52 for spraying recirculated water into tank 28. The spraying action of the spray head 52 creates a preferably continuously moving air to water interface within the tank 28 to thereby inhibit the initiation or growth of biological organisms (including microorganisms) or other contamination. This is in contradistinction to a known bladder surge tank (not shown) having a bladder therein which resiliently expands with inflowing water and returns when a water using device draws water therefrom. Dead air spaces abound therein and provide for the proliferation of contaminants and/or microorganisms. In a speculative embodiment, inlet line 49 from main supply connection line 26 may also be connected to a spray head (not shown) such as spray head 52 and/or potentially even be connected to the same spray head 52; but more likely each would be separately coupled to distinct spray heads (not shown).

A pressure valve 60 is preferably disposed in the shunt feedback line 40, the pressure valve being situated to control the pressure in the outlet flow lines from pump 32. A pressure sensor/control assembly 61, including a sensor gauge 63 is preferably disposed on valve 60 to sense the pressure in line 40, as well as in the output line 31 and the initial portion of line 33 up to filter 70 (if used, see below). A line extension member 62 extends from the valve 60 through an opening 68 into storage tank 28 for flowing water from loop 40 into the interior of tank 28 through valve 60. The pressure in line 40 controls the activation (restriction) of valve 60, or more appropriately, the control assembly 61 may be used to set the pressure to be established in line 40 and the pump outlet line 31, 33, which pressure is effected by the valve 60, controlling the pressure out of pump 32. The pressure gauge 63 may also be used for operator monitoring of the interior pressures in lines 31, 33 and 40 and a relief valve 64 may also preferably be supplied to relieve excess pressures. An optional, but preferred downspout 65 is shown in dashed lines in FIG. 3 demonstrating the option of feeding water into tank 28 for dispersal at or near the bottom thereof to counteract vortex creation as will be described further below.

In the respective tank outlet and sub-system circulation lines 30 and 33, a few additional preferred elements are also shown in FIG. 3. Two valves 67 and 69 are shown one each on opposite sides of the pump 32 and may be used to provide for controlling the flows out of the tank 28 and into the circuit sub-system 25. A stopcock 45 is also preferably disposed in line 30 to allow for draining water on the inlet side of pump 32, for maintenance, inter alia.

A filtration device 70 is also shown in sub-system supply line 33 and is preferably used here to ensure that the water flowing through the sub-system 25 remains free of contaminants. Two pressure sensors 72, 74, one on each side of the filter 70, are used for monitoring and thus also assisting in maintaining proper control of the transmembrane pressure thereof. Adjacent stopcocks 76, 78 may be used both during priming and/or for taking test samples as may be desired or necessary (see below). Filtration device 70 may be of several types preferably restricting the transmission of microorganisms and as is preferable herein, it may be an ultra-filtration device, preferably dead-ended as understood in the art, with no cross-flow established through the dead-ended inlet 80A and outlet 80B, respectively.

In a general description of use, the sub-system 25 of any of FIGS. 1–3 receives water from the main water supply system 10 (FIGS. 1 and 2) through inlet line 26 from main system line 14. This water then fills tank 28 to a preferred level, as described above, with water then also proceeding out through the tank outlet line 30 (if and when valve 67 is opened; FIG. 3). This outlet water is then preferably pumped by pump 32 into and through the sub-system supply line 33. And, when connected to one or more high-demand machines 20B, preferably through a respective valve 39 (FIG. 3) at a branch 34, then during operation of these high-demand machines 20B, they draw the water they need from line 33 through the respective one or more branch connections 34 and corresponding valve(s) 39. If sub-system supply line 33 is not dead-ended (as shown with a preferred feedback loop 38 and the optional drain line 36 in FIG. 3), then the unused water flowing through sub-system supply line 33 flows to and through the chosen alternative line path open thereto, drain line 36 or, more preferably in normal operation through the recirculation loop line 38, for example. Drained water, which would alternatively flow through drain line 36, would then discharge to a sewer system (or to other optional locations or apparatuses, e.g., it could flow back to the R/O unit 12, not shown). On the other hand, unused water flowed into and through the preferred recirculation loop 38 will flow to and through the recirculation inlet line 41 into tank 28, which as above, preferably includes a spray head connection 52 for spraying the inlet recirculation water into the tank 28.

Referring now again to FIG. 3, a more detailed description of the use of sub-system 25 will be presented. Purified water flows into sub-system 25 via inlet line 26 as connected by connection member 42 to the main system supply line 14 (FIGS. 1 and 2), preferably via a mating connection member 43 (FIG. 3). A check valve 44 ensures forward one-way flow only into sub-system 25 and the flow control valve 46 allows for a controlled maximum flow rate of the water into the sub-system 25. When the unit is connected to the main line 14 via connector 42, water flow may then be allowed to proceed into tank A float valve 50 can be used to stop inflow of water when a pre-selected water level has been reached inside tank 28. Outlet flow from tank 28 proceeds through outlet line 30 to pump 32 which then pumps the outlet water to and through outlet and supply lines 31, 33, respectively. When in use, water may and preferably is also pumped through recirculation shunt line 40 back to recirculate into tank 28. Flow through this line 40 may be operator-controlled as well by a shutoff or three-way valve (not shown). However, the preferred use of shunt line 40 provides the user the ability to set the pressure that is supplied to the high demand dialyzer reprocessing equipment through the flow from pump 32 to and through the sub-system line 33. The pressure regulator assembly 61 can be set to an operating pressure according to preferred reprocessing equipment manufacturer instructions (typically 30 to 40 pounds per square inch (psi)), with the regulated pressure being controlled by the valve 60 and indicated on the pressure gauge 63 attached to the pressure regulating valve assembly 61. Water will then flow from the pump 32 in a continuous loop through this loop 40 and also then into and through sub-system line 33 under a substantially common pressure set by the pressure regulating assembly 61 (with a controlled transmembrane pressure drop across filter 70). In either event, control over the operation of pump 32 may be additionally aided by the two flow valves 67, 69 on the respective upstream and downstream sides of pump 32, to shut-off flow as may be desired.

Flow through the sub-system supply line 33 preferably receives one more purification step by flow through the dead-ended ultrafiltration device 70. Pressure sensors 72 and 74 are used to ensure that the pressures therein (particularly the transmembrane pressure thereacross) do not exceed pre-selected levels. Though not their primary purpose (which is sampling), stopcocks 76, 78 may also be used in the monitoring and pressure control processes by providing for relieving excess pressures or pressure differentials as they may occur. As shown, filter 70 is the last mechanical processing element in the flow path prior to the water use machine outlets 34. This may thus provide further assurance of water purity prior to actual use in the high demand machine or machines 20B. An unshown alternative placement of filter 70 is in branch line 31 leading out of pump 32 prior to the branch off shunt line This placement would further ensure purification of water shunted through loop 40 as well.

As mentioned, purified water exiting the filter 70 shown in FIG. 3, then travels along supply line 33 and branches therefrom through a respective branch connection 34 when a demand for water is presented by a high demand device 20B connected thereto, the respective valve 39 also being opened to permit flow therethrough. Used water then flows out of that device 20B through the drain line 21 preferably to the sewer system (not shown).

Unused water at this point then travels preferably, as shown in FIG. 3, through a recirculation loop 38 back to storage tank 28 via the inlet line 41 and spray head 52. The spray action creates a preferably constantly moving air to water interface within tank 28, especially along the interior surface thereof. Such movement assists in reducing the likelihood of biological growth inside the tank 28. Preferably also, some unused water is simultaneously recirculated through shunt line 40. Pressure valve 60 is used primarily to control the pressure of the fluid in outlet flow line 31 and the supply line 33, at least in that portion of supply line 33 which is directly upstream of filter 70. Then, so long as the pressure drop across the membrane is sufficiently managed (through monitoring thereof using gauges 72, 74), then the pressure of the water flow through all of supply line 33 can be controlled to present the proper operating pressures to the high demand device(s) 20B connected thereto. Note, during operation, recirculation is preferably constant through both feed back lines 38 and 40 and pump 32 continually running regardless whether high demand device(s) 20B are drawing water therefrom. Moreover, flow into tank 28 through line 26 from main line 14 will preferably be more intermittent wherein it is substantially constant until a minimum level of water is achieved in tank 28 (even with water preferably continually being pumped therefrom into the rest of the circuit sub-system 25), but, then is turned off by the float valve 50 until a sufficient draw by one or more devices 20B sufficiently lowers the operating volume in tank 28. Such substantially constant recirculation flow may, as preferred, enter tank 28 both near the top of tank 28 through a spray head 52 (from loop 38, e.g.) and simultaneously dispersed in or near the bottom of tank 28 (from loop 40, e.g.) for the purposes described above.

The intended purpose for the entire supply sub-system 25 is as a "buffer" between a main supply line 14 fed by a treatment (e.g., reverse osmosis (R/O) or de-ionization (DI)) machine 12 providing water at a constant rate, and one or more dialyzer reprocessing machines 20B and/or other machine processes consuming water at a variable and intermittently high rate. The reuse supply sub-system 25 receives water from the R/O unit 12 at a constant rate into a relatively small, preferably about a 30-gallon reservoir 28 and, by means of a pump 32 (preferably a centrifugal type) and a pressure control mechanism (see pressure regulating valve/assembly 60/61), provides this water to dialyzer reprocessing machines 20B at a constant pressure and variable rate. Even so, the output capacity of the R/O machine 12 would still preferably exceed the combined consumption rates of all dialysis applications (machines 20A) and the average consumption rate of all dialyzer re-processing applications (machines 20B) operating simultaneously.

The reuse supply sub-system 25 is preferably to be connected to a purified water distribution main system (see system 10, FIG. 1) that supplies water meeting current Association for the Advancement of Medical Instrumentation (AAMI) requirements for dialyzer reprocessing (i.e., "AAMI Standard") and other AAMI requirements as applicable (e.g., hemodialysis machines and hemodialysis concentrate) as applicable.

In preferred operation particularly in a dialysis setting, the AAMI standard water enters the sub-system 25 through a two-piece stainless steel coupling known as a "quick disconnect" including the water inlet connection 42 and the corresponding outlet connection device 43. The main water distribution (R/O) side of the quick disconnect preferably has a "female" connector 43 with an internal shut-off valve (not shown), while the reuse supply sub-system side of the quick disconnect has a "male" connector 42 with or without an internal shut-off valve. After passing through the quick disconnect, water next flows through a check valve 44. The check valve 44 prevents inadvertent back-flow of water or disinfectant chemicals from the reuse supply sub-system 25 into the purified water distribution system 10.

Water next flows through flexible tubing line 26 and passes through a flow control valve 46. The flow control valve 46 regulates water flow into the reuse supply sub-system 25 at a rate that does not exceed R/O unit output capacity. Typically, the flow control valve 46 regulates flow to approximately one and one-half (1.5) gallons per minute (gpm), although other sizes may be provided according to individual requirements and capacities.

Inlet water next passes through a float valve 50 before entering the tank 28. The float valve 50 controls the maximum level or height to which the tank 28 can be filled. Once the tank 28 is full to the preferred, predetermined level, the float arm assembly 51 will shut off the incoming water supply to the tank 28.

The tank 28 is preferably constructed of polyethylene, has a respective concave (dished) top and bottom, and a preferred maximum capacity of about 30 gallons. The tank stand (not shown) is preferably non-metallic and includes a pump mounting surface directly below the tank 28. The top of the tank 28 has a larger (e.g., six inch) threaded access port 55 that is hermetically sealed closed preferably by a correspondingly sized (e.g., six-inch) threaded PVC cap preferably sealed with Teflon tape on the threads. This opening is provided as a service and assembly access port. It should not be opened under normal circumstances, and should remain closed during operation to ensure a leak-proof and airtight seal. There is also a preferable two-inch port 56 fitted with a levered male cam lock and dust cap connector (not shown in detail). The levers on the dust cap would allow it to be easily opened and closed. This port 56 provides easy access for adding chemical disinfectants to the sub-system 25. Properly attached, the dust cap makes an airtight seal. Other elements adjacent and/or connections to the top of the tank 28 are preferably disposed at the spray head inlet line 41, the Pressure Relief Valve (PRV) inlet line 62 and the vent connection for the 0.2 micron air vent filter 52. At the bottom of the tank 28 is a preferable one-inch piping line connection from which water flows from the tank 28 into water line 30 and the inlet to the pump 32.

At the bottom of the tank 28 is a valve 67 that when opened allows water to flow to the pump 32. This valve 67 is primarily an aid for servicing purposes and is not preferably used during routine operations. The pump 32 is preferably yet only typically capable of pumping up to 10 gallons per minute at 45 pounds per square inch (psi). Other pumps, larger or smaller, may be used to provide for various flow and/or pressure requirements; for example, 15 gallons may also be typical in a cleaning/sterilizing environment for medical or other high quality uses. The output line 31 of the pump 32 is then preferably connected to a tee fitting to split flows through sub-system supply line 33 and recirculation shunt loop 40.

Thus, one side of the tee junction directs flow through shunt line 40 to a Pressure Relief Valve (PRV) 60 and pressure regulating assembly/gauge 61/63. In the preferred embodiment, connected to extension line 62 inside the tank 28, is a downspout 65 (shown in dashed lines), which directs the flow to the bottom of the tank 28 and disperses it to prevent formation of a vortex (swirling). This may also help to avoid the possibility of air getting into the pump 32 via such a vortex. The PRV assembly 61 allows the user to set the pressure that is supplied to the dialyzer reprocessing equipment 20B via line 33. The regulator should be set according to reprocessing equipment manufacturer instructions, typically 30 to 40 psi (taking into account any pressure drop between the pump 32 and the outlet(s) 34, e.g., across filter 70), with the regulated pressure being indicated on the pressure gauge 63 attached to the PRV assembly 61. Water will flow in a continuous loop through the flow path defined by the loop 40. Flow path 40 also preferably includes a stainless steel female quick disconnect connection member 66, also referred to herein as the recirculation connector 66, for use during rinse and disinfection procedures (to be described below).

The other side of the tee junction out of pump 32 and line 31 directs flow through a sub-system supply line 33 which preferably includes a FiberFlo (tm) hollow fiber cartridge filter 70 (available from the Minntech Corp., Minneapolis Minn.) and then to outlets for one or more dialyzer reprocessing machines 20B, a drain valve/line 37/36 (dashed lines), a recirculation loop 38, and then back into the tank 28 via a spray head assembly 52. The first component downstream of the tee branch junction is a valve 69 that can isolate flow from the storage tank 28 and PRV recirculation shunt path 40 from the dialyzer reprocessing equipment outlets 34. This is followed by a pre-filter pressure gauge 72, used to measure pressure at the inlet of the filter 70. A sample port 76 has been placed at or near the filter inlet to permit pre-filter sample collection. The preferred filter 70 is the FiberFlo filter introduced above, 20 long (nominal) and is constructed of polysulphone hollow fibers rated by the manufacturer to remove both bacteria and bacterial endotoxin. The cartridge-style filter 70 can be removed from the housing and replaced during routine maintenance or when microbial or delta pressure monitoring (transmembrane pressure taken from gauges 72 and 74) indicates a need for filter replacement. The filter housing includes connections and/or sample ports 80A and 80B at the top and bottom to either vent or flush the housing (and could alternatively be used in an ultrafiltration manner to provide a flow of a clean fluid on the on the opposing side of the membrane therein, though not preferable here). A sample port 78 has been placed at or near the filter outlet to permit post-filter sample collection and follows (or may be followed by) a post-filter pressure gauge 74. The pre- and post-filter pressure gauges permit filter pressure drop monitoring/measurements (an indicator of either fiber breakage or plugging) as well as of the pressure being supplied to the reprocessing outlets 34. Although the order of these outlets may vary, the first few outlets 34 following the filter assembly 70 may preferably be valved outlets for pre-rinse, clean sink (clean water) connections. Then, the next one or more outlets 34 are preferably valved outlets for dialyzer reprocessing equipment 20B. Lastly, preferably the drain valve 37, closed during normal operation, would allow for the operator to drain the tank 28. Then, water returns to the tank 28 via the recirculation loop 38 and the spray head assembly 52.

Various ancillary preferred operating procedures for the preferred dialysis reuse machine sub-system 25 in connection with a main circuit 16 will now be described.

The following is a system start-up procedure, which presumes power to the pump 32 is turned off, the tank 28 is empty, and has been disinfected and rinsed.

First, the drain valve 37 should be verified as closed. Then, the inlet waterline 26 is connected to the water supply quick connection via connect devices 42/43. The tank 28 will begin to fill. Then, after the tank 28 is approximately one-third (⅓) full, the pump switch may be turned to the on position, allowing the pump 32 to run and circulate water. Pressure readings across the filter 70 and at the pressure regulator gauge 63 should be verified that they are within specifications. The tank will continue to fill until the level is maintained by the inlet float valve 50.

Then, at the end of the desired period of operation, a system shutdown procedure includes draining the tank 28 as now described after each desired period (e.g., a day) of use. In particular, draining the tank includes disconnecting the inlet water line from the main line 14 by disconnecting member 42 from member 43 and then connecting the inlet water line 26 to the recirculation connector 66 for connecting the sub-system 25 the position shown in FIG. 4. Then, the pump 32 is turned on and the drain valves 67 and 37 are opened; and, the tank level is observed. Then, after the water drains out of the tank 28, the pump 32 is turned off. Note, the pump 32 should not be run after the tank 32 has been drained, as air could then enter the pump 32, and then damage to the pump 32 may result.

The reuse supply sub-system 25 should preferably be left with the water supply quick connection 42 plugged into the recirculation connector 66 at the end of each period's (e.g., day's) use. Overflow of the tank 28 or damage to the reuse supply sub-system 25 may result if in instances where an R/O system has the capacity for heat disinfection and if the water supply quick connection 42 is left connected to the R/O main line distribution loop 16.

Another set of ancillary procedures includes disinfection and cleaning. In exterior cleaning, the unit 25 should first be unplugged from the power (preferably 120V) connection (not shown). Then, non-electrical exterior surfaces may then be cleaned preferably with a 1% Renalin(tm) or other peracetic acid cleansing solution. A spray disinfectant solution should not be sprayed on the power switch, motor or like electrical components. These may be wiped with a damp cloth containing water only.

Figure 4:
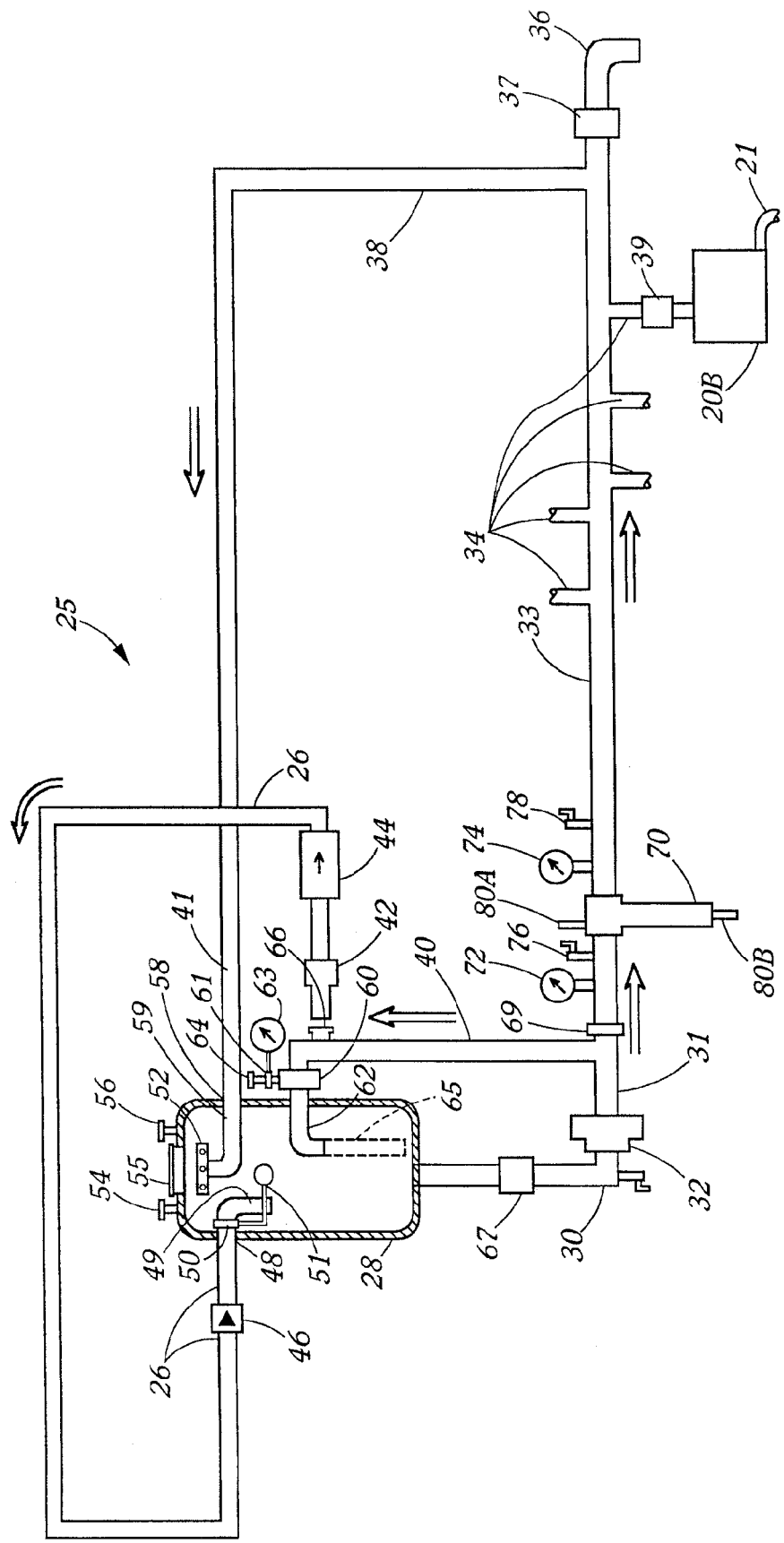
FIG. 4 is a schematic view of a sub-system like that in FIG. 3 showing a further alternative line connection.

In periodic, preferably weekly, disinfection of the tank 28 and fluid pathways (pipe or tubing lines); first the tank 28 should be drained or filled, as needed, so that the tank level is preferably approximately one-third (⅓) full. (If draining the tank 28, it will be preferred and/or necessary to disconnect the water inlet line 26 from the main water supply 14 (to halt further inflow from main line 14), and then reconnect it to the recirculation connector 66 in shunt loop 40; see FIG. 4.) Then, the power to the pump 32 should be turned off, and, the inlet water line 26 should be verified as connected to the recirculation connector 66 as shown in FIG. 4 and the drain valve 37 as closed. Then, the cap to the disinfection port 56 at the top of the tank 28 is removed, preferably by lifting the locking arms (if such a mechanism is used) on the sides of the cap. Preferably, approximately one-half (½) a quart of Renalin or like peracetic acid disinfectant is poured into the tank 28 through the access port 56. It is cautioned that appropriate Personal Protection Equipment (PPE) should be used to prevent peracetic acid exposure to skin or eyes. Then, the disinfection port cap is replaced over the port 56 and locked in place by pressing the locking arms (if used) down all the way. Again, other locking means may be used to lock the disinfectant access port cap onto/over the port 56, preferably in an airtight sealed relationship.

Next, the pump 32 will be turned on, and the sub-system 25 should be allowed to recirculate, preferably for about a minimum of five (5) minutes. A small container (not shown) may then be placed under the pre-rinse and/or clean water connections (i.e., the preferable first one or more connections 34 after the outlet from filter 70; also known as spigots 34A, or valved spigots 34A; see FIG. 4), and then the valved spigots 34A slowly opened to allow the disinfectant to flow out of the each such spigot 34A. A hose (not shown) attached to each such spigot 34A may also be used. These last few spigot opening steps should then be repeated for any other valved connections on line 33, including any clean water spigot (not separately shown), or any such connections 34 (see FIG. 3, e.g.), including the re-use connections 34, particularly those not connected to a re-use or other high demand machine. However, the opening of the valved connections 34 which are connected to a re-use machine (such as connection 34B connected to machine 20B in FIG. 4) may also be desirably opened to run disinfectant solution therethrough at this point in the procedure as well, even though the disinfectant solution would then be destined to be flowed into the high demand machine 20B (disinfection thereof would follow the manufacturers" suggestions/requirements, but could be run simultaneously or close in time with disinfection of the rest of the sub-system 25).

To then conclude the circulation of the disinfection solution through sub-system 25, first a test of the solution potency or concentration at the sample port 78 downstream of the filter 70 and the pre-rinse and clean water spigots 34A is run using a test strip recommended by the peracetic acid manufacturer. The results of this test are recommended to be positive (≧500 ppm of peracetic acid). Then, the pump 32 can be turned off, and the sub-system 25 may now be allowed to dwell for a down/inoperative period, such as overnight or for over-the-weekend storage. The minimum dwell time for storing the sub-system 25 filled with peracetic acid solution is preferably about two (2) hours.

The following tank and fluid pathways rinsing steps may then be followed after disinfection (and a preferable minimum dwell time, e.g., 2 hours; see above), assuming preferably that the above disinfection solution circulation steps (or the like) had previously been taken.

The operator first verifies that the inlet water line 26 is connected to the recirculation connector 66, as shown in FIG. 4. Then, the tank 28 is drained using the following sub-steps. The pump 32 is turned on, the drain valve 37 is opened, and then, the tank level is monitored, until the water and disinfectant solution is drained out of the tank 28. Then, the pump 32 is turned off, again cautioned to not run the pump 32 after the tank 28 has drained, as damage to the pump 32 may result.

Next, the inlet water line 26 is connected to the main water supply line 14 via the quick connection member 42 at a branch 18 (see completed schematic connections in FIGS. 1 and 2, e.g.). Then, the tank 28 will begin to fill with purified water from the purified water main system 10 through line 26. The sub-system drain line 37 is also closed. The tank 28 is allowed to fill until it is approximately one-third (⅓) full (the tank drain valve 67 may also be closed temporarily during initial filling process, then opened). Then, the pump 32 is turned on.

The pre-rinse and clean water spigots 34A (see FIG. 4) are next opened briefly to allow some fresh water to flush through these spigots 34A. A container or a hose (neither shown) may be used (or needed) to catch the water leaving each such spigot 34A if it is not so situated as to drain directly into a sink or like receptacle (not shown). The drain valve 37 is then opened. And, the tank level is then monitored. After the water drains out of the tank 28, the pump 32 is turned off. Again, the pump 32 should not be operated after the tank 28 has drained, as damage to the pump 32 may result. These last several steps (from filling the tank 28 and rinsing through the sub-system 25) are preferably repeated until a negative test (≦3 ppm of the disinfectant cleaning solution, such as Renalin or equivalent peracetic acid) for the presence of the disinfectant solution (Renalin/peracetic acid) is obtained at the post-filter 70 sample port 78 and/or the pre-rinse and clean water spigots 34A, or the like.

The following disinfection steps are particularly additionally applicable when using a portable R/O unit (not separately shown) as the main supply system purification unit 12 (see FIG. 1). The portable R/O unit 12 should first be verified as turned off. The reuse supply tank 28 should then be drained as indicated in the steps set forth above (turning on the pump 32, opening the drain valve 37 and monitoring the tank level). Then, a disinfection procedure of the portable R/O unit 12 may be performed preferably per the manufacturer's guidelines. Peracetic acid based disinfectants should preferably be used. Then, upon completion of the portable R/O disinfection process, the reuse supply tank 28 is drained of any water that may have entered the tank 28 as a result of the portable R/O disinfection process. Then, the reuse supply tank 28 and the rest of sub-system 25 are disinfected and rinsed as described above.

Various preferred maintenance procedures will now be described.

The steps for replacing the preferred filter 70 will now be described. When, as measured by the respective pressure gauges on opposing sides of the filter 70, the differential (transmembrane) pressure across the preferable membrane (hollow fiber, plate or otherwise) filter 70 exceeds the manufacturers" recommendation, or a recommended time period has been reached, or when microbial monitoring indicates the desirability thereof, the filter 70 may be changed as follows. (Note, the preferred filter 70 is a FiberFlo Hollow Fiber Cartridge filter, manufactured by the Minntech Corporation, Minneapolis, Minn. FiberFlo is a registered trademark of the Minntech Corp. Hollow fiber cartridge filters of this type have also been known as ultrafiltration devices or ultrafilters, and such and other alternative filters are also intended to be useful herein as well.) First, the sub-system supply tank 28 should be drained and/or at least the valve 67 may be closed. The filter 70 housing can then be drained using the connection spigot 80B at the bottom of the housing. The filter 70 housing can then be opened and the filter membrane can be removed (in the preferred FiberFlo filter, a simply removable and replaceable cartridge simplifies this removal). A filter wrench (not shown) may make it easier to open the housing. A new filter membrane (and/or cartridge) may then be installed and the housing closed and sealed shut. The inlet water line 26 may then be connected to the main water supply line 14 via the quick connector device 42 at a branch 18 as described above. The tank 28 is then filled, preferably to about one-third (⅓) full, at which point the pump 32 is preferably turned on. The filter 70 is then preferably flushed according to manufacturer guidelines. A disinfection procedure may then preferably be performed of the sub-system supply tank 28.

The replacement of the preferred vent filter 54 is manufacturer recommended at a replacement interval of six (6) months when used regularly in the application described herein above. The preferred vent filter 54 is a five (5) inch 0.2 micron vent filter is manufactured by Waterlink Technologies of West Palm Beach Fla. The replacement includes the draining of the re-use supply tank 28 first, and then includes unscrewing the filter housing (not separately shown) and removing the filter. Then the new filter is installed and the filter housing is replaced and tightened.

The pressure regulator adjustment process usually involves filling the tank 28 until it is at least about one-third (⅓) full and then turning the pump 32 on. The regulator 61 may then be adjusted until the pressure reading on the PRV gauge 63 reads the preferably pressure for supply to the supply line 33 and the high-demand machines 20B; here, preferably about thirty to forty (30–40) psi.

A preferred long-term storage procedure will now be set forth. The tank 28 should first be disinfected per the above instructions, leaving a 1% peracetic acid disinfectant solution in the tank 28 and in the fluid pathways 26, 30, 31, 33, 38, and 40, inter alia. The pump 32 may then be unplugged from the power (120V) connection (not shown). The 1% peracetic acid disinfectant solution may preferably be replaced every two weeks per above instructions. For storage intervals greater than one (1) month, the system should be fully drained of liquid and the FiberFlo filter 70 removed. Upon removal from this storage, a new FiberFlo filter 70 should be installed and then the system should be disinfected again per the above instructions.

Various warnings and/or cautions should now be addressed. For example; the reuse supply system may preferably be disinfected with Renalin, Minncare (tm) (Renalin, Minncare, and FiberFlo are registered trademarks of Minntech Corporation, Minneapolis, Minn.) or other peracetic acid solutions of like concentration that have been diluted in a ratio of 1:100 with purified water meeting the current requirements of the Association for the Advancement of Medical Instrumentation (AAMI) for dialyzer reprocessing. Always follow manufacturer's recommendations for the handling, storage and use of peracetic acid solutions, including those given for potency and residual testing.

And, as a point of caution, it should be noted again that the pump 32 should not be operated with an empty tank 28. Operation of the pump 32 with an empty tank 28 will damage the pump unit.

Also, various alternative embodiments may be available. In one or more alternative embodiments (not shown), the two recirculation loops 38, 40 may be connected to each other prior to entrance into the tank 28. Thus, they could then both be connected to a spray head 52 or to a mere inlet extension 62 or even to a downspout 65. Nevertheless, such a connection is not preferred because the separate functionalities of both the spray head 52 (agitating the water/air surface in tank 28) and the downspout 65 (counteracting any vortex action at the exit from tank 28) are preferably retained in the preferred embodiment. Furthermore, the outlet pressure of pump 32 is controlled by the pressure regulating valve/assembly 60/61. In another alternative embodiment, the recirculation loop(s) 38, 40 could be connected to inlet line 26, and then the recirculation inlet to tank 28 could be defined as identically indistinct from the primary inlet 48. Thus, there could be only one inlet line, with the recirculation line(s) connected to the main supply connection line 26. However again, the separate functionalities of the separate inlets is preferred. Note, as preferred, the inlet flow from the main line 14 through line 26 is controlled to a maximum draw rate from line 14 by the control valve 46, and this inlet flow will preferably be stopped by the float valve 50 when a sufficient maximum volume is detected in the tank 28. However, it is preferred that during operation, a continuous flow of water cycles through the feedback loops 38, 40 to provide a continuous spray of water spraying through spray head 52 and a continuous vortex counteraction from downspout 65 (so air does not reach pump 32).

Moreover, as a further aid to prevention of microbiological growth, an alternative embodiment ultrafiltration device (not shown), perhaps like ultrafilter 70, may be disposed in and adjacent either of the tank inlets for recirculation lines 38, 40 just prior to re-entry of recirculating water into tank 28. Disposition in either or both of these inlet lines provides for ensuring the purification of the water recirculated through either recirculation loop 38 or shunt 40. Otherwise, similar ultrafilters could separately be placed in other locations in either or both of these recirculation loops 38 and/or 40. Another alternative placement of an ultrafilter 70 is in pump outlet line 31 to ensure contamination free flow after pump 32 regardless whether the flow is shunted through line 40 or run through supply line 33, drained or looped back through line 38. However, outlet pump pressure control using a pressure regulating valve/assembly 60/61 would not be a direct control if situated downstream of such a filter 70, and may not be as effectual as in the preferred embodiment. Furthermore, depending primarily upon capacity, parallel dispositions of ultrafiltration devices such as device 70 may be established to ensure a sufficient quantity of flow through the filtration portion of the sub-system circuit.

A couple of further possible alternatives could involve pump controls (not shown). For example, high and/or low water sensors disposed inside the tank 28 could signal respective high and or low water levels which could then be converted into control signals to either turn the pump 32 on or off. For example, a low water sensor (not shown) could be disposed to sense when too little volume remains inside tank 28, and therefore sends a signal which is ultimately used to turn the pump 32 off (effectively, a low-water cut-off device to stop the pump). A pump protective higher sensor in tank 28 could then be used to indicate that a sufficient minimum quantity of water is disposed inside tank 28 so that it would be safe (low or no opportunity for air entry therein) then to turn on pump 32. The signal could itself be converted to control pump 32. A similar high water level sensor could similarly be used in lieu of (or as a fail safe in addition to) the float valve 50 to halt flow into tank 28. As a more particular (yet, non-limiting) example of this, a sensor and valve configuration could be used to actually halt the flow of water into the tank at a high level point. A normally closed valve (e.g., a valve which is closed when no power is provided thereto) may be used in conjunction with a high level sensor such that when no water is in contact with the sensor, power is allowed to be continually provided to the valve so that the valve is in an open state to provide continual inflow of water into the tank. Then, when the tank fills sufficiently such that water does reach and contact the sensor, the sensor provides a signal (preferably through a relay or like device) to halt power to the valve, which then closes and thereby stops flow of water therethrough and into the tank. Such a valve could also be connected to the power supply to entire system, whereby halting such power to the overall system, would then also cut off power to the valve so that the valve then closes. This could then act as a failsafe in case overall power is unexpectedly lost, and/or could act as a regular (e.g., nightly) flow stoppage mechanism, for example, when operation is to be ended at the end of each day, then turning off the overall power will then shut the valve off and stop the flow of water into the tank. In this way, then, water flow in loop 16 need not be stopped at the end of each day, nor would system 25 need to be disconnected therefrom, even if loop 16 is disinfected or otherwise has other flows therethrough after normal operation.

The pump 32 could also have characteristics allowing for increasing pump output if it sensed that the re-use or like high demand machines 20B were demanding such quantities of water that they might overwhelm the present pump output. The pump may then include the necessary internal elements for sensing the need for a greater output, and/or there could be disposed certain pressure and/or flow meters or the like (not shown) in the respective flow lines, e.g., sub-system supply line 33, to provide feedback to the pump 32 to start, stop or change output, positively or negatively as needed.

The present invention may take many forms in distribution or the like. For example, the present invention may involve distribution of a sub-system kit, which may be incorporated later in/on an otherwise substantially independent main water supply system. Advantages in expense and/or automation may be realized here. Alternatively, the sub-system may be manufactured and distributed as part of an entire water supply system, which includes the main supply line with or without water purification devices.

As noted, systems of the present invention may be highly beneficial in numerous water supply systems including those requiring purified water such as in medical applications like dialysis, or may also be useful in pharmaceutical preparation or electronics manufacturing or other water supply processes. In each of these or other uses, the present invention handles the delivery of water in a main loop for relatively low, often substantially constant demand devices together with the delivery through a sub-system of relatively higher demand water usually at more intermittent intervals. It should also be noted that the present invention may be used with or without purification water supply systems.

Also, though it may be noted that the present invention handles pressure fluctuations, which may be incurred by having both low and high demand water using devices on a water supply line; the present invention may also be directed to handling other water handling issues as well. For example in the medical dialysis field, heat issues may be handled by the present invention. Heat sterilization of a main water supply line or loop is common in the dialysis water supply field; however, heat sterilization processes are not compatible with state-of-the-art re-use machines. The present invention effectively isolates the reuses machinery from the main loop so that the re-use machines are not exposed to the high temperature water (or other fluid) flowing through the main loop. Similarly, it is common situation that re-use machines are preferably disinfected using a chemical solution or disinfectant, and the present invention provides an isolated ability to provide such a chemical to the re-use and/or other dialyzer pre-use cleaning or like equipment connected to the sub-system. The chemical solution or disinfectant may be placed in the smaller storage tank of the sub-system and circulated throughout the sub-system as shown for example in FIG. 4 in an isolated manner separately from the disinfection/sterilization process of the main system (which as described here, could be heat-based).

Accordingly, a new and unique invention has been shown and described herein which achieves its purposes in an unexpected fashion. Numerous alternative embodiments readily foreseeable by the skilled artisan, which were not explicitly described herein are considered within the scope of the invention which is limited solely by the claims appended hereto.

What is claimed is:

1. A water supply sub-system for connection to a main water supply system, said sub-system comprising:
    a storage tank having an inlet for connection to said main water supply system, and an outlet;
    a flow control valve connected to said inlet;
    an outlet line connected to the outlet of said storage tank;
    a pump connected to said outlet line;
    a sub-system supply line connected to said pump, said supply line forming a fluid flow feedback loop to said storage tank;
    at least one branch connection connected to said sub-system supply line;
    a shunt feedback line connected to said pump and to said tank in parallel fluid flow to said supply line;
    a pressure regulatory assembly in said shunt feedback line, and an inlet coupling connected to said inlet adapted to selectively connect or disconnect said inlet to said main water supply system and a mating coupling in fluid communication with said tank, said mating coupling being adapted to selectively receive said inlet coupling, whereby an independent disinfectant system may be established in said sub-system.

2. A sub-system according to claim 1 wherein said mating coupling is in said shunt feed-back loop.

3. A sub-system according to claim 1, further comprising a disinfectant inlet port in said tank.

4. A sub-system according to claim 1 further comprising a check valve in said inlet.

5. A sub-system according to claim 1 further comprising a fluid volume control in said tank connected to said inlet.

6. A sub-system according to claim 5 wherein said fluid volume control comprises an inlet valve and a float arm coupled to said inlet valve.

7. A sub-system according to claim 1 wherein said pressure regulatory assembly further comprises a pressure sensor.

8. A sub-system according to claim 1 wherein said tank further comprises a filtered vent.

9. A sub-system according to claim 1 wherein a water-using device is connectable to said branch connection to receive water from said water supply sub-system.

10. A sub-system according to claim 9 wherein said water using device is a dialysis machine.

11. A sub-system according to claim 1 further comprising a drain connected to said sub-system supply line.

12. A sub-system according to claim 1 wherein said shunt feedback loop is disposed downstream from said at least one branch connection.

13. A sub-system according to claim 1 in which said storage tank has a spray head disposed therein, said spray head being connected to said feedback loop to receive recirculated water therefrom and spray said recirculated water into said storage tank.

14. A sub-system according to claim 1 in which said storage tank has a spray head disposed therein, said spray head being connected to said inlet to said tank and being disposed to spray inlet water into said storage tank.

15. A sub-system according to claim 1 further comprising an ultrafiltration device disposed in said supply line downstream of said pump and upstream of said at least one branch connection.

16. A water supply system comprising
a water processing unit;
a main inlet line connected to said water processing unit;
a main outlet line leading from said water processing unit;
a plurality of main branch connections emanating from said main outlet line; and
a water supply sub-system connected to said main water supply system, said sub-system comprising:
a storage tank having an inlet and an outlet, said inlet being connectable to one of said plurality of main branch connections with an inlet coupling and having a flow control valve connected thereto;
an outlet line connected to the outlet of said storage tank;
a pump connected to said outlet line;
a sub-system supply line connected to said pump;
at least one sub-system branch connection connected to said sub-system supply line;
a shunt feedback line connected between said supply line and said tank;
a pressure regulatory assembly in said shunt feedback line, and
a mating coupling in fluid communication with said shunt feedback line and adapted for selectively coupling with said inlet coupling, forming an isolated sub-system.

17. A water supply system according to claim 16 further comprising a disinfectant access port wherein disinfectant can be circulated in said sub-system when said inlet coupling is connected to said mating coupling.

18. A water supply system according to claim 17 wherein the water processing unit is a water purification device.

19. A water supply system according to claim 17 wherein the water processing unit is a water storage device.

20. A water supply system according to claim 17 wherein a water-using device is connected to one of said plurality of main branch connections emanating from said main outlet line.

21. A method for providing water from a main water supply system to a high demand device without adversely impacting the water flow parameters of the water flowing in said main water supply system, said method comprising,
connecting a supply sub-system to said main supply system, said sub-system comprising:
a storage tank having an inlet for connection to said main water supply system, and an outlet;
an outlet line connected to the outlet of said storage tank;
a pump connected to said outlet line;
a shunt feedback line connected between said pump and said tank; and
a pressure regulatory assembly in said shunt feedback line;
connecting a high demand device to said supply sub-system;
flowing water from said main water supply system and into said sub-system through a flow control valve at a reduced rate such that water pressure in said main supply system is relatively constant;
flowing water in said sub-system to said high demand device for its use; and
controlling water supply to said high demand device by regulating water pressure in said shunt feedback line by using a pressure regulator assembly, and,
at selected intervals, disinfecting the sub-system using a chemical whereby the sub-system is isolated from main supply system during the disinfecting step by disconnecting said inlet from said main water system and connecting said inlet to a high-pressure side of said pump.

* * * * *